United States Patent
Volz et al.

[11] Patent Number: 5,976,079
[45] Date of Patent: Nov. 2, 1999

[54] DEVICE FOR LIFTING THE ABDOMINAL WALL FOR CONDUCTING ENDOSCOPIC EXAMINATIONS INCLUDING SURGERY

[75] Inventors: Joachim Volz, Schreisheim; Mike Klicker, Schiffweiler; Joerg-Uwe Meyer, St. Ingbert; Herbert Schuck, Bliesramsbach; Volker Paul, St. Ingbert, all of Germany

[73] Assignee: Fraunhofer Gesellschaft zur Foerderung der angewandten Forschung e.V., Munich, Germany

[21] Appl. No.: 09/091,769
[22] PCT Filed: Dec. 10, 1996
[86] PCT No.: PCT/DE96/02381
 § 371 Date: Oct. 24, 1998
 § 102(e) Date: Oct. 24, 1998
[87] PCT Pub. No.: WO97/22302
 PCT Pub. Date: Jun. 26, 1997
[51] Int. Cl.[6] .................................................. A61B 17/00
[52] U.S. Cl. ........................... 600/209; 600/206; 600/235
[58] Field of Search .................................. 600/201, 204, 600/206, 209, 235

[56] References Cited

U.S. PATENT DOCUMENTS

| | | |
|---|---|---|
| 5,183,033 | 2/1993 | Wilk ..................................... 600/206 X |
| 5,370,109 | 12/1994 | Cuny .................................... 600/206 X |
| 5,398,671 | 3/1995 | Oritz et al. .............................. 600/204 |
| 5,437,266 | 8/1995 | McPherson et al. ................. 600/235 X |
| 5,573,496 | 11/1996 | McPherson et al. ................. 600/209 X |
| 5,634,882 | 6/1997 | Gagner ................................ 600/209 X |

FOREIGN PATENT DOCUMENTS

WO 91/14392 10/1991 European Pat. Off. .
0 639 348 A1 2/1995 European Pat. Off. .

*Primary Examiner*—Jeffrey A. Smith
*Attorney, Agent, or Firm*—Evenson, McKeown, Edwards & Lenahan, PLLC

[57] ABSTRACT

A device for lifting the abdominal wall for conducting endoscopic examinations and surgery within the abdominal cavity having a handling section and a spiral shaped section which is provided with at least one pitched winding, where the distal end of the spiral-shaped section is provided with a larger spiral diameter than the proximal side.

27 Claims, 2 Drawing Sheets

DEVICE FOR LIFTING THE ABDOMINAL WALL FOR CONDUCTING ENDOSCOPIC EXAMINATIONS INCLUDING SURGERY

BACKGROUND AND SUMMARY OF THE INVENTION

The present invention relates to a device for lifting the abdominal wall for conducting endoscopic examinations, such as surgery within the abdominal cavity. The device has a spiral-shaped section provided with at least one pitched winding and the one end of which is the distal end and which develops on the proximal side into a handling section.

Today, endoscopic instruments meeting ever greater demands for as minimal as possible trauma during surgery are increasingly employed in diagnosis and therapy within the human abdominal cavity. Within the framework of laparoscopy, in order to obtain the freedom of movement necessary for conducting examination and surgical procedures inside an abdominal cavity, the abdominal cavity is filled with gas. The intermediate space, the pneumoperitonium, forming between the internal organs and the abdominal wall due to the selective introduction of gas, has to be maintained over several hours depending on the difficulty and complexity of the surgery to be carried out.

Intra abdominal pressure maintained for an extensive period of time during surgery can lead to diminishment of breathing capacity and, furthermore, to the reduction of venous blood return flow. Moreover, the continuous introduction of gas into the human abdominal cavity, so-called insufflation, leads to slow hypothermia in the patient unless suited tempering of the insufflation gas is attended to during insufflation. In the event of continuous insufflation, hypoxia can set in due to hypoventilation as well as heart rhythm or expectoration disorders connected with the above-mentioned decreased venous return blood flow reduction. Further, intra abdominal pressure conditions can lead to increased vagus irritation due to extension of the peritoneum which, as the lung-stomach nerve, may impair the vegetative nervous system considerably.

Therefore, the question arises whether laparoscopic surgery is possible with reduced pneumoperitonium and whether reduction of intraabdominal pressure, generated and maintained by the insufflation procedure, possesses positive effects on the blood pressure dynamics and the respiratory cycle.

Within the scope of these examinations a number of instruments, with the aid of which the abdominal wall can be lifted manually, have become known as alternative to the aforementioned insufflation technique.

The article "Gasless Laparoscopy and Conventional Instruments" by R. S. Smith et, al., Journal Arch Surg. Vol. 128, Oct. 1993, pp. 1102 to 1107, describes a socalled laparolift system comprising a scissor-shaped mechanism which can be introduced into the abdominal cavity through the abdominal wall in a closed state. Inside the abdominal cavity the two scissor-like limbs can be expanded by means of an expansion mechanism. The two scissor-like limbs lift the abdominal wall from the internal organs by means of external drawing. The fillet like shape of the two scissor-like limbs puts much local strain on the abdominal wall due to the small surface of the support area of the limbs, which may damage the abdominal wall tissue. Furthermore, with lifting the scissor-like limbs, the scissor-like instrument offers only a small tent-like internal space in which endoscopic manipulations and examinations can be carried out only under difficult spatial conditions.

Although, in this manner the disadvantages connected with insufflation are avoided, the method does not ensure a large voluminous inflation of the abdominal cavity in which surgical measures can be conducted without hindering the surgeon.

In order to avoid the disadvantage of only a little expansion of the abdominal cavity achievable with the afore described scissor-like instrument, a spiral-like shaped stainless steel wire construction has been developed. The spiral-shaped state-of-the-art arrangement depicted in FIG. 1 is provided at its distal end E with an essentially centered and parallel to the spiral axis S shaped distal section which is designed on the distal side with a tapering material diameter. On the proximal side, the spiral-shaped section SA develops into a handling section HA, which preferably is composed of the same material as the spiral itself. Starting at the distal end of the spiral-like shaped instrument, the diameter of the spiral widens to a largest value at the point where the handling section HA of the instrument connects to the spiral-shaped section. The spiral-shaped section SA is largely a single winding pitched in the direction of the spiral axis S.

The distal end of the afore described instrument is introduced inside the abdominal cavity through an opening going through the abdominal wall and then is passed intra corporally under the abdominal wall by turning the remaining part of the spiral-shaped section. The handling section HA comprises a fillet St protruding vertically out of the abdominal wall and connected to the handle H. Due to vertical lifting, the inside of the abdominal wall lies on the outer periphery of the spiral-shaped winding and creates a space between the abdominal wall and the internal organs.

Compared to the preceding, scissor-shaped instrument known from the state of the art, the abdominal wall lies on the spiral-shaped section of the instrument over a large area, thereby considerably reducing the pressure strain on the tissue of the abdominal wall. In addition, the circular outer periphery of the spiral-shaped section permits lifting the abdominal wall spatially in such a manner that a larger cavity can be created inside the abdomen for conducting endoscopic surgery.

Apart from the advantages of the designed spiral-shaped instrument over the known methods for expanding the abdominal cavity, there are nonetheless drawbacks connected with it: in view of the fact that the diameter of the spiral widens from the distal end toward the proximal end, in the lifted state the abdominal wall is stretched relatively severely by the outer edge of the spiral, especially because in the area of the almost circular diameter of the spiral, the abdominal wall is lifted over a large area and pulled strongly downward at the edges. In this area, the very great curvature of the abdominal wall very badly strains the tissue. Tissue irritation which can lead to traumatic changes can occur at these sites especially during long surgery.

The centered disposal of the distal end of the spiral shaped section relative to the spiral axis makes this central area within the abdominal cavity not readily accessible for observation endoscopes and endoscopic surgical instruments.

The rigid design of the whole spiral-shaped fabricated instrument makes introduction into the abdominal cavity partly very complicated. In an advantageous manner, a trocar tube, which is pushed into a small opening in the abdomen through which the spiral-shaped section of the described "lifting tool" is guided, is used for the introduction of the distal end inside the abdominal cavity. Practice has shown that the threading into the trocar tube procedure has proven very complicated.

The object of the present invention is to further develop a device for lifting the abdominal wall for conducting endoscopic examinations including surgery inside the abdominal cavity, which device has a spiral-shaped section which is provided with at least one pitched winding and whose one end is the distal end and which develops on the proximal side into a handling section, in such a manner that the aforementioned drawbacks can be eliminated. In particular, the abdominal wall should not be exposed to increased tension during the lifting procedure so that any traumatic tissue changes can be ruled out. Furthermore, the device should create a freely accessible abdomen cavity for the endoscopic instruments so that the surgeon can carry out surgical measures as unimpeded as possible.

An element of the present invention is to develop a device for lifting the abdominal wall for conducting endoscopic examinations including surgery within the abdominal cavity, which device has a spiral-shaped section provided with at least one pitched winding on the distal end with a proximal end opening into a handle, in such a manner that the distal end of the spiral-shaped section in a vertical projection has a larger spiral diameter than the proximal side area of the spiral-shaped section. The distal end of the device may also be flexible.

The present invention is based on the idea that due to the invented shaping of the spiral-shaped section an outer contour which encases this section is created so that the abdominal wall lies on closely and evenly onto the external areas of the individual windings without being subject to major stretching. The outer contour encasing the spiral-shaped section is provided with a relatively dome-shaped outer contour due to which the abdominal wall is not pulled over any edges during lifting.

Widening the diameter of the spiral toward the distal end of the spiral-shaped section permits disposing the distal end required for the insertion procedure not centered to the spiral axis. This makes it possible that the central area of the abdominal cavity is freely accessible for endoscopic aids.

Furthermore, an element of the present invention is that it was understood that adding a flexible section at the distal end region of the device can facilitate the insertion procedure into a trocar tube specially provided in the abdominal cavity. The flexible section is preferably made of a NiTi alloy which is provided with form memory properties and, in addition, has a cross section which resembles a flattened wire. In this manner, the stability properties of the flexible section can be designed differently in various spatial directions.

In order to avoid tissue injury during the introduction procedure within the abdominal cavity, the distal end of the flexible section is rounded off or a ball-shaped element is attached thereto preventing boring into the tissue areas.

BRIEF DESCRIPTION OF THE DRAWINGS

The present invention is made more apparent by way of example in the following using preferred embodiments with reference to the drawing.

DETAILED DESCRIPTION OF THE DRAWINGS

Figure 1:
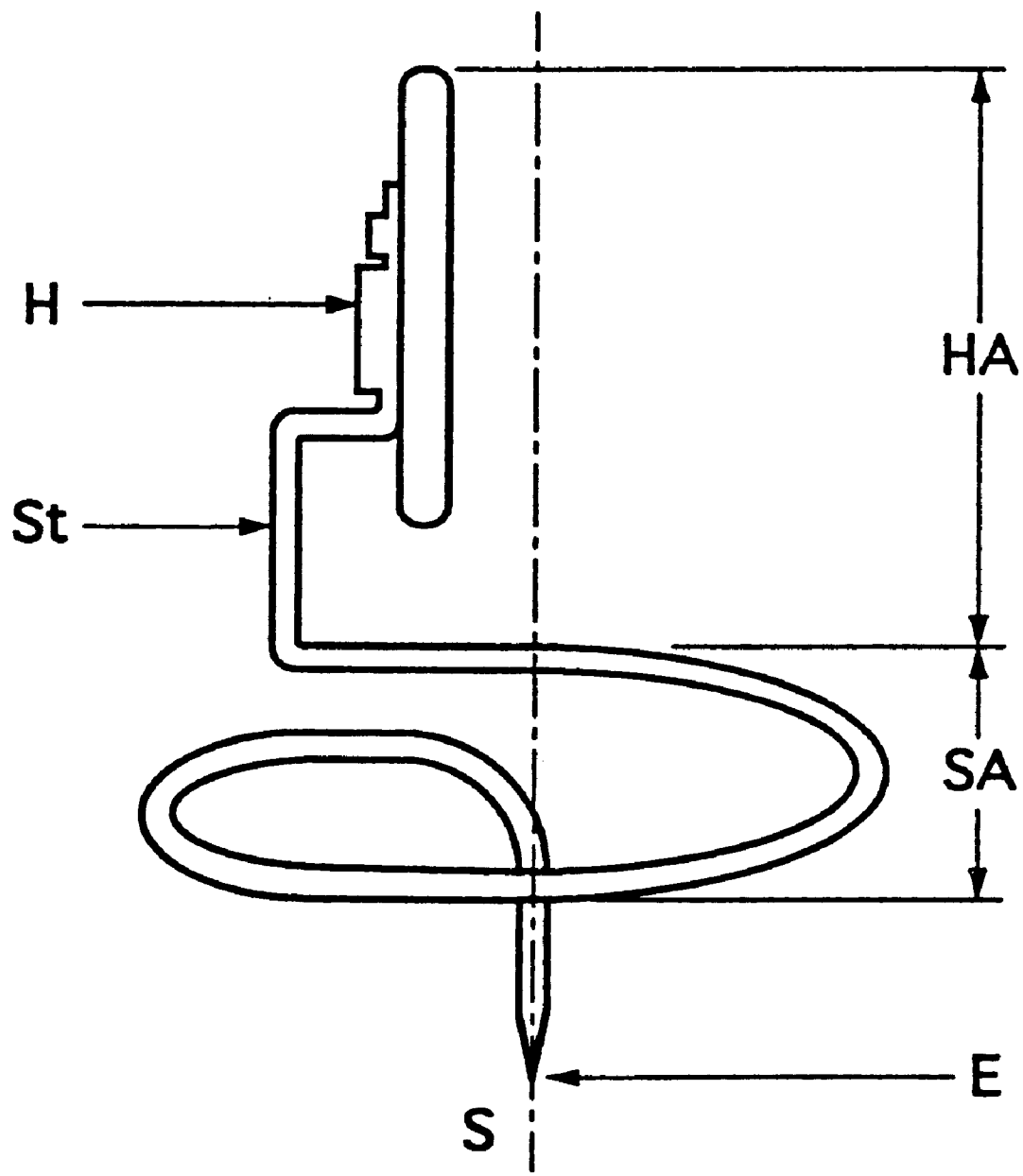
FIG. 1 shows a spiral-shaped lifting device according to the state of the art.
Figure 2:
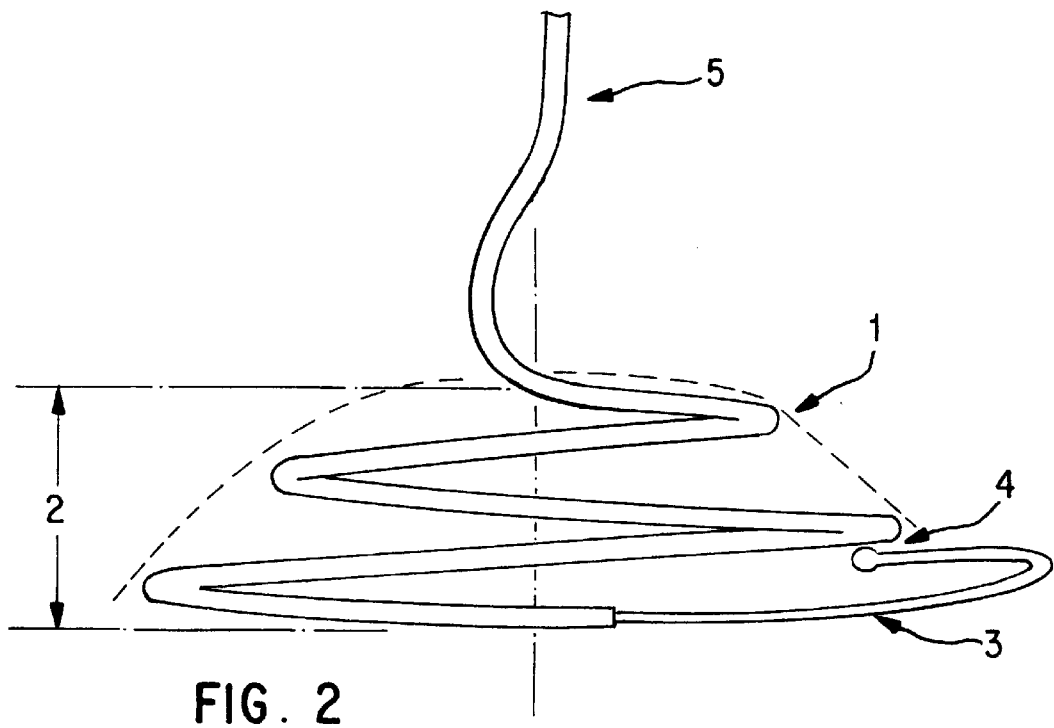
FIG. 2 shows a lateral view of a device designed according to the present invention.

FIG. 2 shows a lateral view of a device designed according to the present invention inserted into the abdominal cavity below the abdominal wall 1. Due to the design of the spiral-shaped section 2 of the device, the abdominal wall 1 lies smoothly dome-shaped around the spiral-shaped section 2. The spiral-shaped section 2 is provided at its distal end with a flexible section 3 which is designed in the extension of the spiral shape with a somewhat smaller winding radius relative to the spiral axis S. In the depicted embodiment, the spiral shaped section 3 is provided with two full windings pitched toward the spiral axis. The spiral-shaped, flexible section 3 is slightly bent counter to the pitch of the spiral-shaped section 2. At its distal end, the flexible section 3 is provided with a ball-shaped section 4 to prevent injury to tissue within the abdominal cavity.

On the proximal side, the spiral-shaped section 2 ends in a handling section 5, which protrudes extra corporally essentially vertically from the abdominal cavity.

All winding radii, both along the handling section 5 and in the spiral-shaped section 3, are to be dimensioned in such a manner that the device can be completely threaded through a trocar tube, not depicted in the figure.

Figure 3:
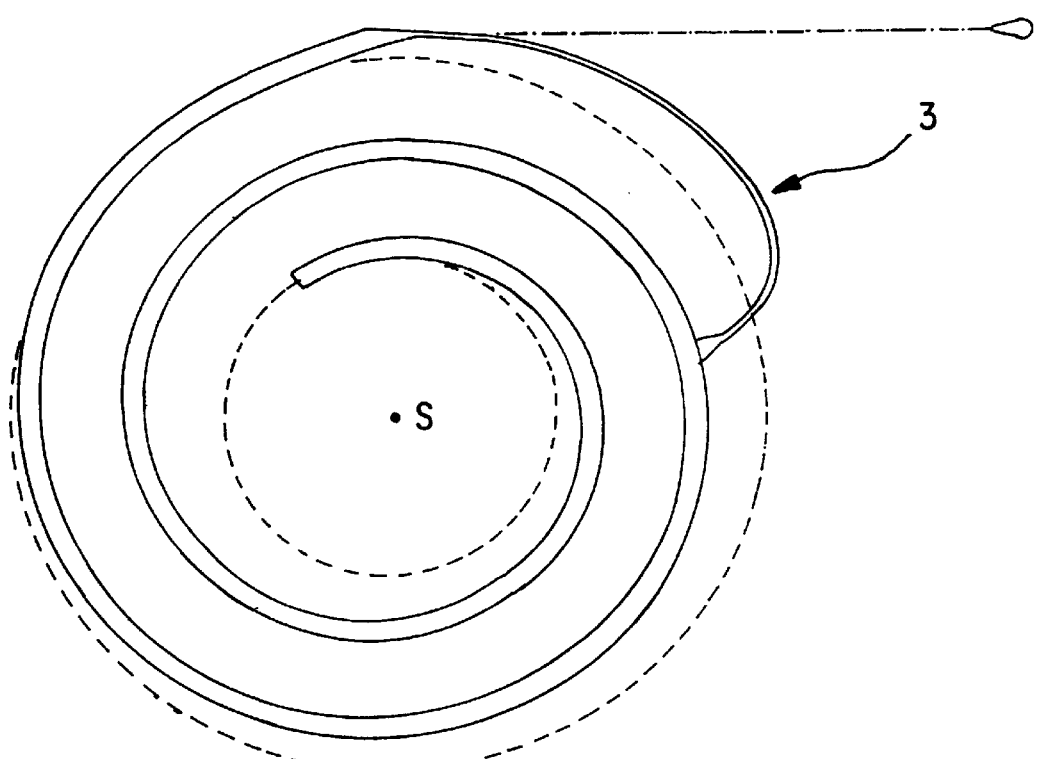
FIG. 3 shows a top view of the device designed according to the present invention.

From FIG. 3 showing a top view of the spiral-shaped section 3 of the invented device, it can be seen that the distance between the individual windings is constant so that an even as possible support area for the abdominal wall on the spiral-shaped section of the device is ensured. The distal end region of the spiral-shaped section 2 is provided with a flexible section 3 which either is made of the same material as the spiral-shaped section 2, only thinned or processed in such a manner that it possesses flexible properties or a nickel-titanium alloy which for example is firmly connected to the spiral-shaped section 2 via a hard soldered joint. Preferably, the handling section 5, which is not depicted in FIG. 2, is designed one-piece with the spiral-shaped section 2. Suited as a material is preferably stainless steel with a diameter of between 4 to 6 mm. On the other hand, the flexible section 3 is provided in an advantageous manner with the cross section of a flattened wire and possesses parallel to the spiral axis S a greater rigidity than vertical thereto.

Advantageously, a transition region is provided between the handling section and the spiral-shaped section and the transition section has flattening windings having winding radii of at least 14 mm.

Also advantageously, the flexible section is more rigid vertical to the axis than the flexible section is rigid horizontal to the axis.

The invented design of the device for lifting the abdominal wall for conducting endoscopic examinations including surgery within the abdominal cavity prevents the raised abdominal wall from being exposed locally to moments of extreme stretching and, in addition, the flexible design of the distal end region of the flexible section 2 facilitates insertion into a trocar tube.

What is claimed is:

1. A device for lifting the abdominal wall for conducting endoscopic examinations or surgery within the abdominal cavity, the device comprising:

a spiral-shaped section having an axis and being provided with at least one pitched winding, the spiral shaped section having a distal end and a proximal side, said proximal side developing into a handling section, wherein said distal end of said spiral-shaped section in vertical projection to the axis is provided with a larger spiral diameter than said proximal side of said spiral-shaped section, wherein the handling section is connected in one-piece to the spiral-shaped section, wherein a transition region is provided between the handling section and the spiral shaped section and the transition section has flattening windings having winding radii of at least 14 mm.

2. The device according to claim 1, wherein the at least one pitched winding of the spiral shaped section has a pitch in the direction of the distal end.

3. The device according to claim 1, wherein the spiral-shaped section has a dome-shaped outer contour.

4. The device according to claim 1, wherein the device is made of stainless steel.

5. The device according to claim 1, wherein the device is insertable into a trocar tube.

6. A device for lifting the abdominal wall for conducting endoscopic examinations or surgery within the abdominal cavity, the device comprising:

a spiral-shaped section having an axis and being provided with at least one pitched winding, the spiral shaped section having a distal end and a proximal side, said proximal side developing into a handling section, wherein said distal end of said spiral-shaped section in vertical projection to the axis is provided with a larger spiral diameter than said proximal side of said spiral-shaped section, wherein the distal end has a flexible section.

7. The device according to claim 6, wherein a distal end of the flexible section is rounded or terminates in a ball.

8. The device according to claim 6, wherein the flexible section is composed of a NiTi alloy.

9. The device according to claim 6, wherein the flexible section is provided with a cross section of a flattened wire.

10. The device according to claim 6, wherein the distal end region is provided with a greater curvature toward the spiral axis than the remaining area and is slightly formed counter to the pitch of the spiral-shaped section.

11. The device according to claim 6, wherein the flexible section and the spiral-shaped area are firmly connected by a hard soldered joint.

12. The device according to claim 6, wherein the device is insertable into a trocar tube.

13. The device according to claim 6, wherein the flexible section is more rigid vertical to the axis than the flexible section is rigid horizontal to the axis.

14. The device according to claim 6, wherein the at least one pitched winding of the spiral shaped section has a pitch in the direction of the distal end.

15. The device according to claim 6, wherein the spiral-shaped section has a dome-shaped outer contour.

16. The device according to claim 6, wherein the device is made of stainless steel.

17. The device according to claim 6, wherein the handling section is connected in one-piece to the spiral-shaped section.

18. The device according to claim 17, wherein a transition region is provided between the handling section and the spiral shaped section and the transition section has flattening windings having winding radii of at least 14 mm.

19. The device according to claim 6, wherein the device is insertable into a trocar tube.

20. A device for lifting the abdominal wall during endoscopic examinations and surgery within the abdominal cavity, the device comprising:

a spiral-shaped section provided with at least one pitched winding, the spiral-shaped section having a distal end and a proximal side, the proximal side developing into a handling section, wherein the distal end has a flexible section.

21. The device according to claim 20, wherein the flexible section has an end that is rounded or terminates in a ball.

22. The device according to claim 20, wherein the flexible section is composed of a NiTi alloy.

23. The device according to claim 20, wherein the flexible section is provided with a cross section of a flattened wire.

24. The device according to claim 20, wherein the distal end is provided with a greater curvature toward the spiral axis than the remaining area and is slightly formed counter to the pitch of the spiral-shaped section.

25. The device according to claim 20, wherein the flexible section and the spiral-shaped area are firmly connected by a hard soldered joint.

26. The device according to claim 20, wherein the device is insertable into a trocar tube.

27. The device according to claim 20, wherein the flexible section is more rigid vertical to the axis than the flexible section is rigid horizontal to the axis.

* * * * *